(12) United States Patent
Dhamane et al.

(10) Patent No.: US 11,491,175 B2
(45) Date of Patent: Nov. 8, 2022

(54) SYNERGISTIC BIOACTIVE COMPOSITIONS FOR ENHANCING CELLULAR ENERGY

(71) Applicant: CELAGENEX RESEARCH (INDIA) PVT. LTD., Maharashtra (IN)

(72) Inventors: Dhiraj Dhamane, Kalyan-Thane (IN); Rajendra Prasad Tongra, Jaipur (IN)

(73) Assignee: CELAGENEX RESEARCH (INDIA) PVT. LTD., Thane (IN)

( * ) Notice: Subject to any disclaimer, the term of this patent is extended or adjusted under 35 U.S.C. 154(b) by 0 days.

(21) Appl. No.: 17/433,575

(22) PCT Filed: Feb. 25, 2020

(86) PCT No.: PCT/IN2020/050170
§ 371 (c)(1),
(2) Date: Aug. 24, 2021

(87) PCT Pub. No.: WO2020/174492
PCT Pub. Date: Sep. 3, 2020

(65) Prior Publication Data
US 2022/0125815 A1     Apr. 28, 2022

(30) Foreign Application Priority Data
Feb. 25, 2019 (IN) .............................. 201921007187

(51) Int. Cl.
*A61K 31/708*   (2006.01)
*A61K 31/706*   (2006.01)

(52) U.S. Cl.
CPC .......... *A61K 31/708* (2013.01); *A61K 31/706* (2013.01)

(58) Field of Classification Search
CPC .......................... A61K 31/706; A61K 31/708
See application file for complete search history.

(56) References Cited

U.S. PATENT DOCUMENTS

| 4,459,292 A | 7/1984 | Andermann |
| 5,602,105 A | 2/1997 | Karsanov |
| 2018/0071273 A1 | 3/2018 | Horn |

FOREIGN PATENT DOCUMENTS

| CN | 103550242 A | | 2/2014 |
| EP | 3342414 A1 | | 7/2018 |
| FR | 2518882 A1 | | 7/1983 |
| RU | 2240116 C1 | | 11/2004 |
| RU | 2414896 C1 | | 3/2011 |
| WO | 2006086454 A2 | | 8/2006 |
| WO | WO2014096958 | * | 6/2014 |
| WO | 2017024255 A1 | | 2/2017 |
| WO | 2017033963 A1 | | 3/2017 |

OTHER PUBLICATIONS

RU2414896C1, google translation, original document published in 2011; six pages (Year: 2011).*
Sigma Aldrich "Disodium Inosinate"; https://www.sigmaaldrich.com/US/en/substance/disodiuminosinate39217anhydrousbasis352195405; obtained Mar. 3, 2022 (Year: 2022).*
Barbara A. Moffatt et al. Apr. 4, 2002 The *Arabidopsis* Book—Purine and Pyrimidine Nucleotide Synthesis and Metabolism.

* cited by examiner

*Primary Examiner* — Bahar Craigo
(74) *Attorney, Agent, or Firm* — Maschoff Brennan

(57) ABSTRACT

The present invention relates to synergistic bioactive compositions for enhancing cellular energy in aerobic or anaerobic conditions. Particularly, the invention relates to a synergistic bioactive composition comprising specific combination of purine nucleoside and hydrophilic pyridinecarboxamide compound(s) which are present in the ratio of 1:0.1 to 1:1 along with pharmaceutically acceptable carriers/excipients, wherein 'purine nucleoside' is inosine adduct and the hydrophilic pyridinecarboxamide compound is selected from nicotinamide riboside or nicotinamide mononucleotide either alone or in combination thereof. Further, the present cellular energy enhancing bioactive compositions are useful for treating ATP deficiency conditions. Moreover, the composition is useful for treating hepatic dysfunctions.

8 Claims, 3 Drawing Sheets

SYNERGISTIC BIOACTIVE COMPOSITIONS FOR ENHANCING CELLULAR ENERGY

TECHNICAL FIELD OF THE INVENTION

The present invention relates to synergistic bioactive compositions for enhancing cellular energy in aerobic or anaerobic condition.

Particularly, the invention relates to synergistic bioactive compositions comprising combination of purine nucleoside and hydrophilic pyridinecarboxamide compound(s) along with pharmaceutically acceptable excipients, wherein purine nucleoside is 'inosine adduct' and hydrophilic pyridinecarboxamide compound is 'nicotinamide mononucleotide' or 'nicotinamide riboside' either alone or in combination.

Further, the present cellular energy enhancing bioactive compositions are useful for treating disorders with ATP deficiency. Moreover, the composition is useful for enhancing hepatic ATP turnover.

BACKGROUND AND PRIOR ART

The mitochondria is a double-membrane-bound organelle and is considered as the energy factory of cells Adenosine triphosphate (ATP) is the main energy carrying molecule and is produced in the mitochondria using energy stored in food. ATP is the key source of energy for most cellular processes. The building blocks of ATP are carbon, nitrogen, hydrogen, oxygen, and phosphorus.

ATP production by the mitochondria occurs via cellular respiration, which combines oxygen with nutrients/glucose from the food molecules to generate energy. The process can be represented as, glucose+oxygen→carbon dioxide+water. The energy derived from the breakdown of the chemical bonds in nutrients/glucose is ultimately conserved in the high energy phosphate bonds of ATP. When these bonds are broken, they provide accessible energy to cells, tissues, organs and organ systems. This is a very efficient process for using food energy to make ATP. ATP can be produced either aerobically through oxidative phosphorylation, with oxygen as the terminal electron acceptor and yielding carbon dioxide ($CO_2$) and water as by-products, or anaerobically during glycolysis. While glycolysis can provide energy to cells, the supply is limited because the cellular environment becomes acidic, injuring the cell and inhibiting ATP production.

ATP plays a critical role in the transport of macromolecules such as proteins and lipids into and out of the cell. Because of the presence of unstable, high-energy bonds in ATP, it is readily hydrolyzed in reactions to release a large amount of energy. The hydrolysis of ATP provides the required energy for active transport mechanisms to carry such molecules across a concentration gradient. Transport of such molecules into the cell is called endocytosis whilst transport out of the cell is known as exocytosis.

Since ATP is a primary source of energy for cells, increased metabolic demand or deficit in the supply of ATP to cells can result in death of the cells if demand is not met quickly.

ATP deficit is related to various metabolic dysfunctions such as hemolytic anemia, sickle cell disease, pyruvate kinase deficiency, spherocytosis, elliptocytosis, stomatocytosis, thalassemia, nerve injury, oxidative stress, inflammation, muscle pain, hypoxia, cardiac cirrhosis, Ischemic hepatitis, fatty liver, liver cirrhosis, heart failure, ischemia-reperfusion insults, diabetic, stroke, spinal cord injury etc.

Additionally, intracellular ATP reduction is suggested as a mechanism of myocardial damage due to ischemic heart disease.

According to the research, an ATP enhancement therapy is likely to be effective for controlling muscle, brain, liver and heart related disorders. It can be expected that enhancing ATP through de novo or salvage pathway improves pathological conditions of diseases in which a decrease in ATP relates to the pathological conditions.

The nucleotide and nucleosides of a cell are continually in flux. DNA and RNA chains are being synthesized in the cell. Even though the overall DNA content of a cell is constant, small stretches are continually being repaired. Part of the repair process is the breakdown of one strand of the DNA double helix into nucleotides, nucleosides, and free bases. Free purines and pyrimidines are converted back into nucleoside triphosphate monomers to be reincorporated into DNA.

Purine nucleotides are involved in many cellular functions as components of DNA and RNA, sources of energy, enzyme cofactors in metabolic pathways, and components of signal transduction.

There are two principal routes for the synthesis of nucleotides (FIG. 1): the de novo and the salvage pathways. Using 5-phosphoribosyl-1-pyrophosphate (PRPP), the de novo pathway enzymes build purine and pyrimidine nucleotides from "scratch" using simple molecules such as $CO_2$, amino acids and tetrahydrofolate. This route of nucleotide synthesis has a high requirement for energy as compared that of the salvage pathway. For example, five of the 12 steps of de novo purine synthesis require hydrolysis of ATP or GTP but only one salvage cycle reaction uses ATP. The enzymes of both of these biosynthetic routes are classified as "housekeeping" enzymes because they perform basic, cellular activities and are assumed to be present in low, constitutive levels in all cells. Whereas the de novo pathway is thought to reside in plastids, salvage cycle enzymes may be localized in more than one compartment [Barbara A. Moffatt et al. Apr. 4, 2002 *The Arabidopsis Book—Purine and Pyrimidine Nucleotide Synthesis and Metabolism*]. An increased level of PRPP is characterized by the overproduction and accumulation of uric acid leading to hyperuricemia and hyperuricosuria. It is one of the causes of gout.

Salvage pathways are used to recover bases and nucleosides that are formed during degradation of RNA and DNA. This is important in some organs because some tissues cannot undergo de novo synthesis. The de novo purine synthesis pathway requires several moles of ATP for generation of each mole of purine nucleotide product. It is observed that more cellular energy is conserved in the purine salvage in comparison with the de novo purine synthesis pathway and 90% of free purines generated during intracellular metabolism are recycled rather than degraded or excreted. Moreover, salvage pathways economize intracellular energy expenditure.

Further salvage pathways are considerably more energy-efficient than de novo pathways, which require less moles of ATP for each mole of nucleotide produced. Salvage pathways are integral to the cause or treatment of a number of human diseases related to purine or pyrimidine metabolism.

Kam Ming Ko (*Chin Med.* 2007; 2: 3) has reported that ATP generation and its antioxidant and/or immunomodulatory actions on the retardation of aging.

Further Frenguelli B G et al. (*Neurochem Res.* 2017 Oct. 25; 44(2): 507, 2017) discloses the combined effect of ribose, adenine (RibAde), and allopurinol, for accelerating ATP synthesis and increasing the reservoir of the neuroprotective metabolite, adenosine, that help to reduce the morbidity associated with stroke and traumatic brain injury.

'Inosine', also known as hypoxanthine riboside is produced in the human body, and its chemical structure is related to adenosine, which is included in adenosine triphosphate (ATP), which is the energy source during the work done by each muscle.

It is observed that nucleotide biosynthesis carried out through salvage pathway is an energy saving route, where first purine nucleotide synthesized is inosinic acid (IMP), this nucleotide can serve as a precursor for both AMP and GMP synthesis. The synthesis of AMP from IMP and the salvage of IMP via AMP catabolism have the net effect of deaminating aspartate to fumarate. This process has been termed the purine nucleotide cycle. This cycle is very important in muscle cells. Increases in muscle activity create a demand for an increase in the TCA cycle, in order to generate more NADH for the production of ATP. However, muscle lacks most of the enzymes of the major anaplerotic reactions. Muscle replenishes TCA cycle intermediates in the form of fumarate generated by the purine nucleotide cycle.

Inosine, the primary byproduct of adenosine, which is considered as relatively either inactive or weak metabolite and hence has been somewhat "brushed aside," from last decades. Yet, it should be remembered that inosine has been used as an inotropic agent for more than 20 years in several countries (France, Germany, Japan, Russia) due to its capacity for increasing cardiac output without chronotropic effect and increase of myocardial oxygen consumption.

Inosine is known to have cell energizing activity. Due to its known medicinal benefits, the products containing inosine are marketed for, restoring nerve function, improving the heart's energy production and athletic performance and muscle development. These products include InoCare®, REMAXOL®, CYTOFLAVIN® Injections and RIBOXIN®, Novirin® Inosine Tablets.

Inosine combinations are also reported in some prior arts, like US20040192553A1 discloses Inosine and L-Arginine salt compositions for cell activation and/or plant growth promotion.

EP3342414A1 discloses human intracellular ATP enhancer comprising a combination of a xanthine oxidase/ xanthine dehydrogenase inhibitor and inosine, inosinic acid, hypoxanthine, and pharmaceutically acceptable salts thereof.

FR2518882A1 discloses therapeutic composition, based on inosine monophosphate, for the treatment of eye disorders such as strabismus, presbyopia, heterophoria etc.

CN103550242A mentions pharmaceutical oral composition containing pirfenidone and inosine for treating liver fibrosis, liver fibrosis, cirrhosis, liver cancer.

WO02017033963A1 reports intracellular ATP enhancer composition comprising a combination of a febuxostat and inosine, wherein the composition is useful to a patient with hemolytic anemia, ischemic heart disease, heart failure, amyotrophic lateral sclerosis, Parkinson's disease, or Adenylosuccinate lyase (ADSL) deficiency etc.

Furthermore, it is reported that administration of inosine alleviates symptoms of Parkinson's disease and Multiple sclerosis. It is believed that a decrease in serum uric acid value may be related to the diseases. Clinical trials have been conducted by administering inosine to raise the serum uric acid value and produce a therapeutic effect. It has been reported that intracellular ATP somewhat increases due to single administration of inosine. However, inosine is rapidly metabolized in human bodies through hypoxanthine and xanthine to uric acid. Therefore, inosine alone is insufficient to produce the sufficient ATP enhancing action.

However, higher dosages of inosine and its solubility in water limit the scope of inosine as a therapeutic agent.

Accordingly, there is a need in the art to develop inosine compositions that can enhance the production of ATP for accelerating rate of cellular growth. The present invention solves this problem and provides a stable and highly effective inosine composition by combining the moiety with pyridinecarboxamide compound which are hydrophilic nicotinamide derivatives to give synergistic effect that maintain intracellular ATP pool or energy pool at desired level.

It is further observed that decline in $NAD^+$ level mediated by commensurate decline in sirtuin signaling can result in functional deficits, such as decreased respiratory capacity and reduced ATP production. Repletion of $NAD^+$, via SIRT activators, can restore mitochondrial structure and protein ratios, leading to increased ATP production. Thus, a key type of age-dependent decline in mammalian tissues may be due to weakness in $NAD^+$ mediated signaling through sirtuins, causing serious consequences in energy physiology and organism fitness.

Moreover, SIRT1 plays as an essential player in regulation of mitochondrial fitness, linked to normal but age-vulnerable NAD+ homeostasis [*Progress in Molecular Biology and Translational Science*, 154, 2018, 71-104].

There are certain prior arts which disclose the therapeutic role of SIRT1 activators particularly nicotinamide derivatives for improving $NAD^+$ level.

US20180071273A1 discloses nutritional composition comprises a synergistically effective amount of a combination of a $NAD^+$ precursor and an ATP booster for treating mitochondrial energy disorders or diseases, wherein the $NAD^+$ precursor comprises at least one of nicotinamide riboside, NAD, nicotinic acid, nicotinamide, nicotinic acid mononucleotide, vitamin B3, nicotinamide mononucleotide or a combination thereof and ATP booster is derived from fruit or fungi source such as apple extract.

WO2017024255A1 relates to compositions of nicotinamide mononucleotide derivatives that promote the increase of intracellular levels of nicotinamide adenine dinucleotide ($NAD^+$) in cells and tissues for treating diseases and improving cell and tissue survival.

WO2006086454A2 discloses nicotinamide riboside or analogs or prodrugs thereof for treating or preventing a disorder associated with cell death or aging in a subject, comprising administering of nicotinamide riboside that increases the flux through the $NAD^+$ salvage pathway or reduces nicotinamide levels in the cells susceptible to or subject to cell death or aging.

LEI LU (*Exp Ther Med.* 2014 September; 8(3): 943-950) has reported that nicotinamide mononucleotide (NMN) may attenuate apoptosis and improve energy metabolism in Parkinson's disease (PD)-like behavioral and neuropathological changes, and produce significant beneficial effects.

In the light of the above cited prior arts, limited work has been done for improvement of rate of cellular growth by ameliorating the production of intracellular ATP and recycling thereof.

The present inventors have performed rigorous experiments to enhance the production of ATP, wherein the active substances can easily generate ATP with less energy consumption. Accordingly, the inventors have developed a composition containing combination of purine nucleoside with GRAS listed, water soluble, pyridinecarboxamide compounds. Interestingly, the pyridinecarboxamide compounds act in a dual manner. They first enhance the solubility of the composition in water and thereby improve the bioavailability of the composition. Secondly, they provide ATP molecules by augmenting $NAD^+$ levels, consequently both moieties synergistically enrich ATP density through energy saving pathway. Finally, the composition is useful for treating various metabolic dysfunctions caused due to loss of ATP.

OBJECTIVE OF THE INVENTION

The primary object of the present invention is to provide a synergistic bioactive composition to control ATP deficiency in the body.

Another object of the present invention is to provide a synergistic composition with high bioavailability for enrichment of intracellular ATP through energy saving pathways which leads to increase in the production of ATP.

Another object of the present invention is to provide biologically safe, water soluble and bioavailable composition of nucleoside for improving cellular health as well as metabolic function.

A preferred object of the present invention is to provide a synergistic combination composition of purine nucleoside and hydrophilic pyridinecarboxamide compounds in an effective amount.

SUMMARY OF THE INVENTION

To meet the above objectives, the inventors of the present invention carried out thorough experiments to establish therapeutic effects of the active ingredients present in the composition that improve ATP deficiency related disorders in a subject in need thereof.

In an aspect, the invention relates to synergistic bioactive compositions for enhancing cellular energy in aerobic or anaerobic conditions.

In another aspect, the invention relates to synergistic bioactive compositions comprising specific combination of purine nucleoside and hydrophilic pyridinecarboxamide compound(s) along with pharmaceutically acceptable excipients or carriers.

In yet another aspect, the invention provides potent synergistic bioactive compositions comprising 'inosine' or adduct thereof as purine nucleoside; and hydrophilic pyridinecarboxamide compound selected from the group consisting of 'pyridine-nucleoside' or 'pyridine-nucleotide' either single or combination thereof; preferably 'pyridine-nucleoside' is 'nicotinamide riboside' (NR) and 'pyridine-nucleotide' is 'nicotinamide mononucleotide' (NMN).

In a further aspect, the invention provides potent synergistic bioactive compositions with improved bioavailability comprising 'inosine' adduct in combination with 'nicotinamide riboside' (NR) and/or 'nicotinamide mononucleotide' (NMN) in therapeutically effective amount.

In one more aspect, the present invention provides synergistic biochemical compositions comprising combination of 'inosine' phosphate adduct and 'nicotinamide riboside'/ 'nicotinamide mononucleotide' for treatment in a subject suffering from ATP deficiency or metabolic dysfunctions or mitochondrial or cellular energy disorders or diseases.

In yet another aspect, the invention relates to synergistic nutritional compositions, wherein 'inosine' is present in the range of 10 to 2000 mg and 'nicotinamide riboside' is present in the range of 1 mg to 500 mg and/or 'nicotinamide mononucleotide' is present in the range of 1 mg to 500 mg along with pharmaceutically acceptable excipients/carriers.

In further aspect, the invention relates to synergistic bioactive compositions, which are useful for treating ATP deficiency or cellular energy disorders, wherein inosine restores formation of ATP by recycling purine bases through salvage pathway, on the other hand pyridine-nucleoside/ nucleotide moiety enhances release of ATP through oxidative phosphorylation in the cell by augmenting $NAD^+$ level.

In another aspect, the present invention provides cellular energy enhancing compositions for mitigating/treating the cellular consequences of nerve injury, oxidative stress, inflammation, hypoxia and ischemia-reperfusion insults, muscle pain, spinal cord injury and other heart, liver and brain related disorders.

Abbreviations:
NMN: Nicotinamide mononucleotide
NR: Nicotinamide riboside
IMP: Inosine 5'-monophosphate/Inosinic acid
HGPRT: Hypoxanthine-guanine phosphoribosyltransferase
ADP: Adenosine diphosphate or Adenosine pyrophosphate (APP)
AMP: Adenosine monophosphate or 5'-adenylic acid
ATP: Adenosine triphosphate
GMP: Guanosine monophosphate or 5'-guanidylic acid or guanylic acid
GDP: Guanosine diphosphate
GTP: Guanosine-5'-triphosphate
$NAD^+$: Nicotinamide adenine dinucleotide (oxidized form)
NADH: Nicotinamide adenine dinucleotide (reduced form).
MTT: 3-(4,5-dimethylthiazol-2-yl)-2,5-diphenyltetrazolium bromide [colorimetric assay]

DETAILED DESCRIPTION OF THE INVENTION

Figure 1:
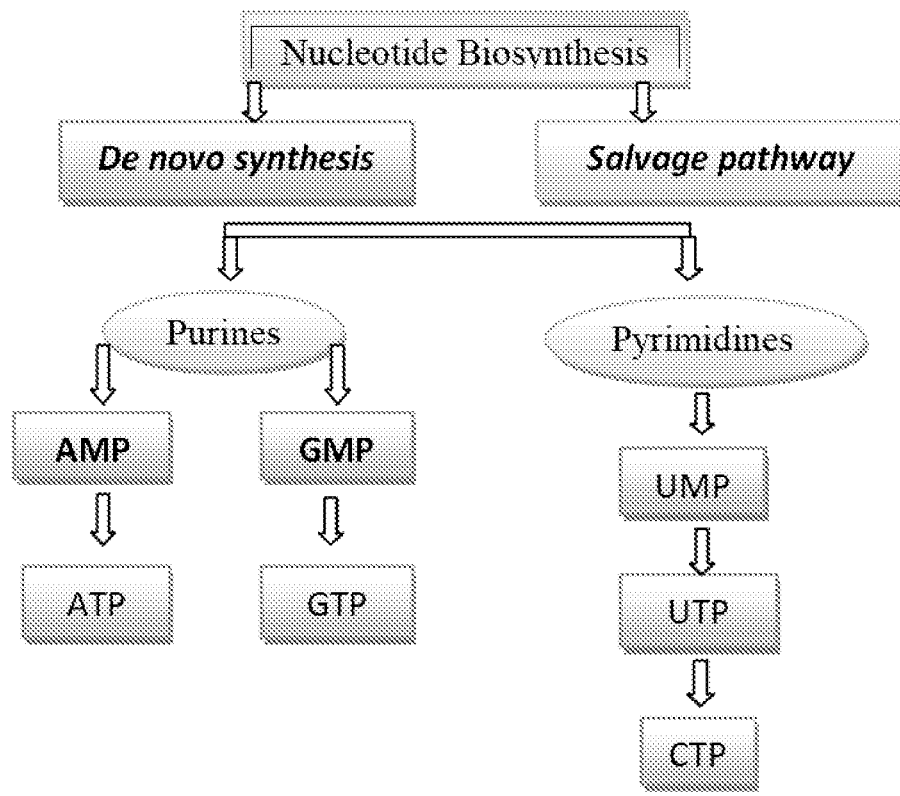
FIG. 1 illustrates the route for biosynthesis of nucleotides through de novo and salvage pathway
Figure 2:
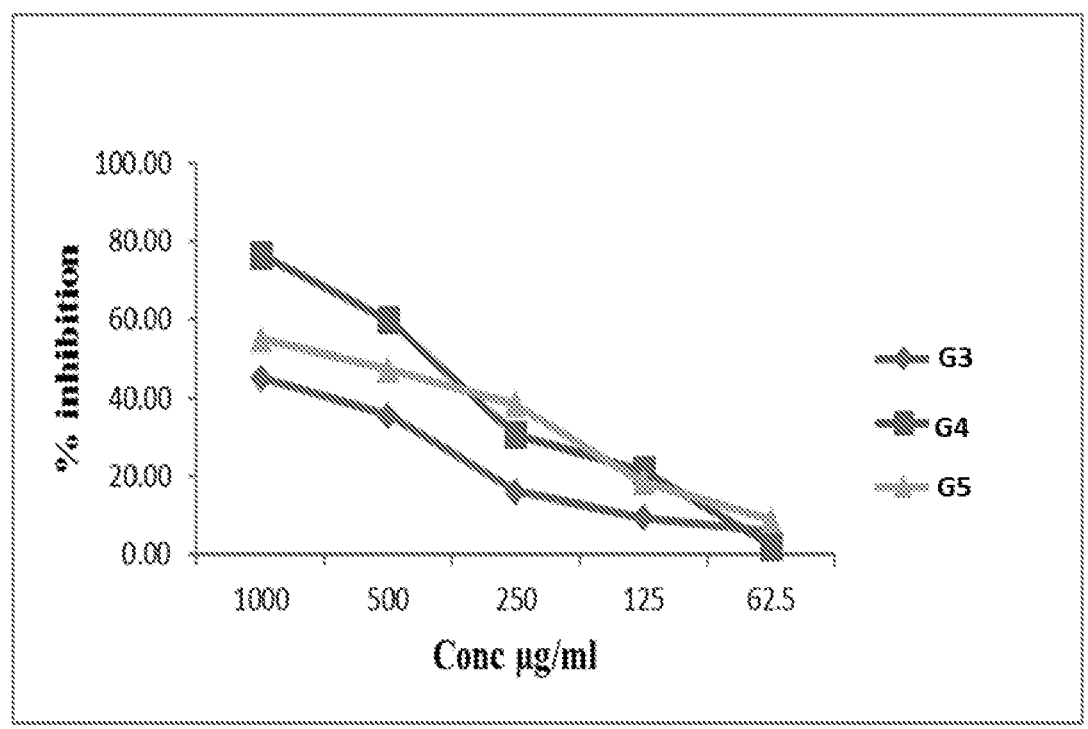
FIG. 2 illustrates the cytotoxic effect of test substances on Human Hepatocyte cells—[G3: IMP, G4: NMN, G5: IMP+ NMN]
Figure 3:
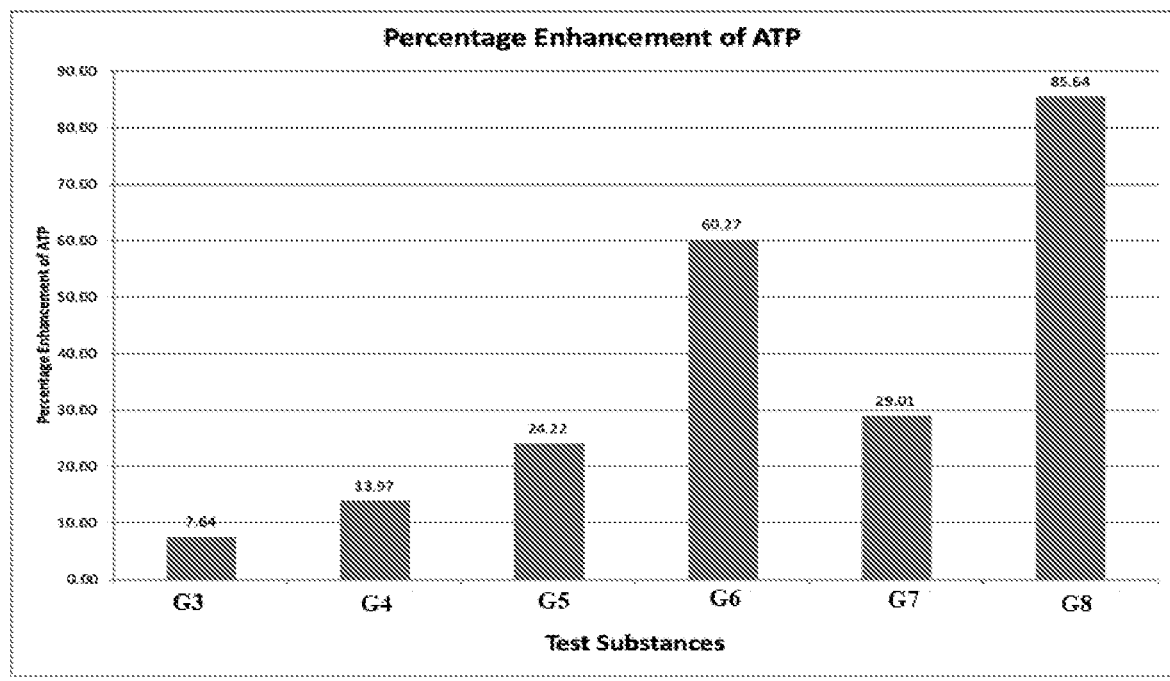
FIG. 3 illustrates the effect of test substances in the enhancement of cellular ATP levels over Hydrogen Peroxide control [G3: IMP (500 ng/ml), G4: NMN (250 ng/ml), G5: IMP+NMN (500 ng/ml), G6: IMP (500 ng/ml)+H2O2 (20 µM), G7: NMN (250 ng/ml)+$H_2O_2$ (20 µM), G8: IMP+ NMN (500 ng/ml)+H2O2 (20 µM).

The invention will now be described in detail in connection with certain preferred and optional embodiments, so that various aspects thereof may be more fully interpreted and comprehended. However, any skilled person or artisan will appreciate the extent to which such embodiments could be generalized in practice.

It is further to be understood that all terminology used herein is for the purpose of describing particular embodiments only, and is not intended to be limiting in any manner or scope.

Unless defined otherwise, all technical and scientific expressions used herein have the same meaning as commonly understood by one of ordinary skill in the art to which embodiments of the invention pertain.

In describing and claiming the embodiments of the present invention, the following terminology will be used in accordance with the definitions set out below which are known in the state of art.

The singular forms "a," "an," and "the" include plural reference unless the context clearly dictates otherwise. Also, the term 'composition' does not limit the scope of the invention for multiple compositions that can be illustrated for best mode of the invention.

The term "pharmaceutically/nutraceutically acceptable salt," as use herein, represents those salts which are, within the scope of sound medical judgment, suitable for use in contact with the tissues of humans and animals without undue toxicity, irritation, allergic response and the like and are commensurate with a reasonable benefit/risk ratio.

Particularly the term "pharmaceutically-acceptable salts" refers to the relatively non-toxic, inorganic and organic acid addition salts of compounds, as well as solvates, co-crystals, polymorphs and the like of the salts.

The term 'nutritional composition' does not limit the scope of the invention only for nutrients but it also includes food supplements, dietary supplements, plant extract, herbal products which are resourced from natural products that eventually contribute to therapeutic effect in a subject.

The term "bioactive" is an alternative term for biologically active. A bioactive compound is simply a substance having therapeutic effect on the living tissue. Particularly a bioactive compound is "a compound which has the capability and the ability to interact with one or more component(s) of the living tissue by presenting a wide range of probable effects". The origin of these substances can be natural: terrestrial or aquatic; a plant, animal or other source (e.g. microorganisms) or synthetic: partially or totally [*International Journal of Nutrition and Food Sciences* 2014; 3(3): 174-179].

In a preferred embodiment, the invention provides synergistic bioactive compositions comprising a specific combination of purine nucleoside and hydrophilic pyridinecarboxamide compound(s) along with pharmaceutically acceptable excipients.

In another embodiment, the invention provides synergistic bioactive compositions, wherein the purine nucleoside is an inosine adduct; and the hydrophilic pyridinecarboxamide compounds are NAD$^+$ precursors.

Inosine [$C_{10}H_{12}N_4O_5$] is a purine nucleoside, which is one of the basic chemicals used to construct cells. L-inosine is the biologically active form. Inosine is formed by attaching a molecule of the purine derivative hypoxanthine to a molecule of sugar ribose via a glycosidic bond. Inosine is commonly found in tRNAs and is essential for proper translation of the genetic code in wobble base pairs. Furthermore, inosine is the precursor for uric acid, which may inhibit the effects of free radicals. Inosine is slightly soluble in water and methanol.

The most common dietary sources of inosine include organ meats, brewer's yeast and yellow lupin.

'Inosine' is also referred to as (−)-Inosine; Hypoxanthosine, Inosina, 1,9-Dihydro-9-β-D-ribofuranosyl-6H-purin-6-one; 9-β-D-Ribofuranosylhypoxanthine; Hypoxanthine ribofuranoside; Hypoxanthine Ribonucleoside; Hypoxanthine Riboside.

In another embodiment, the invention provides the inosine adduct or purine nucleoside in the form of a phosphate salt or a sulphate salt or a complex of inosine, wherein the phosphate salt is selected from monophosphate, diphosphate, triphosphate, and the sulphate salt is selected from monosulphate, disulphate or trisulphate. Further the inosine is used in other acceptable forms such as stereo isomers, conjugates or complex thereof.

In yet another embodiment, the purine nucleoside is selected from the group consisting of inosine 5' monophosphate, inosine 5'-diphosphate, inosine 5'-triphosphate and salts thereof.

In yet another embodiment, the preferable inosine adduct is inosine 5' monophosphate salt, more preferably inosine 5' monophosphate disodium salt hydrate.

In preferred embodiment, the inosine adduct is inosine monophosphate and its metal salt hydrate, preferably sodium salt hydrate.

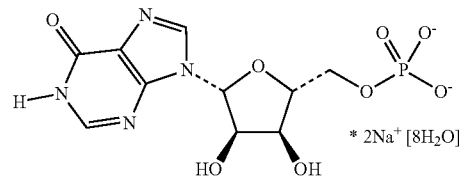

Inosine-5'-monophosphate (sodium salt hydrate)

The administration of inosine phosphate adduct in an effective amount enters in cells through blood. The present inosine composition runs through energy saving salvage pathway, wherein the inosine is metabolically converted to hypoxanthin by the enzyme nucleoside phosphorylase. HGPRT is a transferase that catalyzes conversion of hypoxanthine to inosine monophosphate (IMP) an important purine nucleotide. Lesch-Nyhan syndrome is a severe neurological disorder caused by a deficiency of HGPRT.

Unsalvaged hypoxanthine is oxidized to xanthine, which is further oxidized to uric acid by xanthine oxidase. Molecular oxygen, the oxidant in both reactions, is reduced to $H_2O_2$ and other reactive oxygen species.

Inosinate or inosinic acid or inosine monophosphate (IMP) is the precursor of AMP and GMP. AMP is formed by the addition of aspartate followed by the release of fumarate. GMP is generated by the addition of glutamine and release of glutamate.

Inosine generates ATP through the hypoxanthine-IMP-AMP-ADP-ATP pathway or through the anaerobic pentose pathway. Similarly, Inosine generates GTP trough hypoxanthine-IMP-GMP-GDP-GTP pathway. Further, the GTP production is regulated by ATP content. The biosynthesis of purine nucleotides increases the growth rate mainly through ATP production, which is very useful for developing therapies for malignant neoplasms and for ischemic diseases including brain and myocardial infarctions.

In another embodiment, the invention provides a synergistic bioactive composition, wherein inosine is present in the range of 10 to 2000 mg of total composition. The concentration of inosine adduct is varied based on the equivalent amount of inosine.

In another embodiment, the invention provides a synergistic bioactive composition, wherein hydrophilic pyridinecarboxamide compounds are preferable NAD$^+$ precursors which impart synergy for ATP generation.

In yet another embodiment, the hydrophilic pyridinecarboxamide compounds are NAD$^+$ precursors selected from the group consisting of nicotinamide riboside, nicotinic acid, nicotinamide, nicotinamide mononucleotide, tryptophan alone or combination thereof.

According to the invention, the hydrophilic pyridinecarboxamide compound is selected from the group consisting of pyridine-nucleoside or pyridine-nucleotide, either single or in combination thereof.

In another embodiment, the invention discloses a synergistic inosine composition, wherein the pyridine-nucleoside or pyridine-nucleotide is a hydrophilic nicotinamide derivative or ribose complex of nicotinamide or $NAD^+$ precursors.

In particular embodiment, the $NAD^+$ precursors are selected from group consisting of nicotinamide riboside or nicotinamide mononucleotide and salts thereof either alone or in combinations thereof.

In another embodiment, the hydrophilic pyridinecarboxamide compounds are $NAD^+$ precursors highly or freely soluble in aqueous medium (solubility is more than 1000 ppm), thereby improving the bioavailability of the present composition.

'Nicotinamide Riboside' (NR) is a pyridine-nucleoside form of vitamin B3. Nicotinamide riboside is involved in nicotinate and nicotinamide metabolism. It is a useful compound for elevation of $NAD^+$ levels in humans.

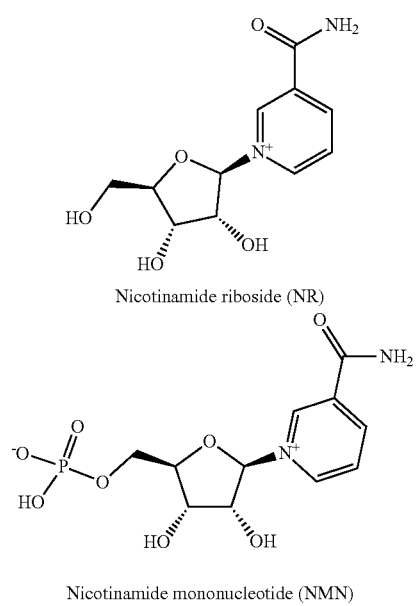

Nicotinamide riboside (NR)

Nicotinamide mononucleotide (NMN)

It is also known as Nicotinamide ribose; Nicotinamide-beta-riboside; Nicotinamide ribonucleoside; N-ribosylnicotinamide; ribosylnicotinamide.

In another embodiment, the invention provides a synergistic bioactive composition, wherein nicotinamide riboside is present in the range of 1 to 500 mg of total composition.

Further nicotinamide mononucleotide (NMN) is an important intermediate metabolite in the nicotinate and nicotinamide metabolism pathway. It is a nucleotide derived from ribose and nicotinamide. Like nicotinamide riboside, NMN is a derivative of niacin, and use to generate nicotinamide adenine dinucleotide (NADH) in presence of certain human enzymes.

Nicotinamide mononucleotide (NMN) is also known as beta-Nicotinamide mononucleotide, beta-NMN, Nicotinamide ribonucleotide, Nicotinamide ribotide, Nicotinamide ribonucleoside 5'-phosphate, Nicotinamide D-ribonucleotide, β-Nicotinamide ribose monophosphate, Nicotinamide nucleotide.

In another embodiment, the invention provides a synergistic bioactive composition, wherein nicotinamide mononucleotide is present in the range of 1 to 500 mg of total composition.

The pyridinecarboxamide compounds, particularly NMN or NR or combination thereof are potential SIRT1 activators easily absorbed from gut into the blood circulation and then into tissues within 15-30 minutes. This absorption of hydrophilic nicotinamide precursors significantly elevates $NAD^+$.

In another embodiment, the invention provides supplementation of insoine along with NAD+ precursors that increases NAD+ availability via the NAD+ salvage pathway.

Further NMN or NR in therapeutically effective amount induces restoration of intracellular levels of $NAD^+$ that account for beneficial effects on the elevation of intracellular ATP generation.

Nicotinamide adenine dinucleotide in its oxidized state is called $NAD^+$, which after reduction (or accepting electrons) is referred to as NADH. NADH is important as it delivers the hydrogens and electrons that it picks up to biochemical processes like ETC (electron transfer chain) that can use the electrons and hydrogens to make ATP.

In yet another embodiment, the present composition comprising effective amount of hydrophilic nictotinamide derivatives preferably NR or NMN or combination thereof, improve mitochondrial function by enhancing ATP energy pool. The administration of effective dose of NR and/or NMN increases $NAD^+/NADH$ ratio in the body to generate an intermediary substance such as AMP or ADP for producing energy in the form of adenosine triphosphate (ATP) from food or nutrients via oxidative phosphorylation.

In another preferred embodiment, the invention provides a synergistic composition of inosine and nicotinamide nucleoside or nucleotide for improving cellular health.

Moreover, the composition comprising inosine monophosphate and nicotinamide riboside/mononucleotide exhibits cell protective and energy restoring effects that can be enhanced, when they are administered simultaneously.

It is noteworthy that present bioactive moieties perform in different intracellular pathways, allowing for complementary biological activities without overlapping. Thus, the combined use of theses bioactive substances become logical and promising for the targeted indication.

It is further manifested that the combinations of IMP and NR or NMN in effective dosage form give synergistic effect in the production of ATP through energy-saving pathways.

In the present invention, the rate of the cellular growth is enhanced by synergistic production of adenosine triphosphate (ATP), wherein exogenous administration of synergistic composition comprising effective amount of inosine monophosphate (IMP) restores ATP level through purine salvage pathway; simultaneously pyridinecarboxamide compounds NR or NMN augment $NAD^+/NADH$ ratio, which leads to increase in the production of ATP through oxidative phosphorylation, thus energy pool is effectively maintained.

In yet another embodiment, the invention relates to synergistic bioactive compositions, wherein 'inosine' is present in the range of 10 to 2000 mg and 'nicotinamide riboside' and/or 'nicotinamide mononucleotide' is present in the range of 1 mg to 500 mg along with pharmaceutically acceptable excipients/carriers.

In one preferred embodiment, the present invention provides synergistic bioactive composition(s) for enhancing cellular energy in aerobic or anaerobic condition, wherein the composition comprises a therapeutic exogenous blend of purine nucleoside and hydrophilic pyridinecarboxamide compound(s) along with pharmaceutically acceptable excipients, wherein purine nucleoside and hydrophilic pyridinecarboxamide compound are present in the ratio of 1:0.1 to 1:1.

In another preferred embodiment, the present invention provides a synergistic bioactive composition comprising purine nucleoside and hydrophilic pyridinecarboxamide compound(s) along with pharmaceutically acceptable excipients, wherein purine nucleoside is Inosine-5'-monophosphate (IMP), and 'hydrophilic pyridinecarboxamide compound(s)' are selected from nicotinamide riboside (NR) or nicotinamide mononucleotide (NMN) and salts thereof either alone or in combination.

Particularly, the Inosine-5'-monophosphate (IMP) is used in form of disodium salt hydrate; NR is used in form of chloride and NMN is particularly used in its stable and active beta anomeric form (i.e. geometric isomer of NMN).

In another embodiment, the present invention provides a synergistic bioactive composition wherein purine nucleoside is preferably Inosine 5'-monophosphate (IMP) disodium salt hydrate and present in the range of 40% to 90% by weight of total blend or composition.

In yet another embodiment, the present invention provides a synergistic bioactive composition wherein hydrophilic pyridinecarboxamide compounds are NAD$^+$ precursors selected from the group consisting of nicotinamide riboside, nicotinamide mononucleotide, nicotinic acid, nicotinamide, tryptophan salts thereof either alone or in combination thereof. Further the hydrophilic pyridinecarboxamide compounds are present in the range of 10% to 35% by weight of total blend or composition.

In one more preferred embodiment, the invention provides synergistic bioactive composition(s) for enhancing ATP content, wherein the composition comprising exogenous blend of Inosine 5'-monophosphate disodium salt hydrate and NAD$^+$ precursors present in the ratio of 1:0.1 to 1:0.5, along with pharmaceutically acceptable excipients. Particularly the NAD+ precursors are nicotinamide riboside chloride or β-nicotinamide mononucleotide either alone or in combination thereof.

In an embodiment, the composition comprises a therapeutic exogenous blend of inosine 5' monophosphate disodium salt hydrate and nicotinamide riboside chloride in the ratio of 1:0.2 to 1:0.5. In an embodiment, the composition comprises a therapeutic exogenous blend of inosine 5' monophosphate disodium salt hydrate and β-nicotinamide mononucleotide in the ratio of 1:0.25 to 1:0.5.

In preferred embodiment, the invention provides a synergistic bioactive composition, wherein the composition comprises exogenous blend of inosine 5' monophosphate sodium hydrate and nicotinamide riboside chloride in the ratio of 1:0.2.

In another preferred embodiment, the invention provides a synergistic bioactive composition, wherein the composition comprising exogenous blend of inosine 5' monophosphate sodium hydrate and β-nicotinamide mononucleotide in the ratio of 1:0.25.

In yet another preferred embodiment, the invention provides a synergistic bioactive composition, wherein the composition comprising exogenous blend of inosine 5' monophosphate sodium hydrate and β-nicotinamide mononucleotide in the ratio of 1:0.5.

In further embodiment, the present invention provides a synergistic bioactive composition, wherein the hydrophilic pyridinecarboxamide compound is beta-nicotinamide mononucleotide (β-NMN) in the range of 15% to 35% by weight of total composition.

In one more embodiment, the present invention provides a synergistic bioactive composition, wherein the hydrophilic pyridinecarboxamide compound is nicotinamide riboside chloride in the range of 10% to 20% by weight of total composition.

In a further essential embodiment, the present invention provides synergistic bioactive composition, wherein the composition comprises a combination of 40% to 90% by weight of Inosine 5'-monophosphate disodium salt hydrate and 10% to 35% by weight of nicotinamide riboside chloride or 15% to 35% by weight of β-nicotinamide mononucleotide along with pharmaceutically acceptable excipients.

In another embodiment, the invention discloses administration of effective dose of present synergistic composition for treating the indications caused due to shortage of cellular ATP content, or the indication caused due to shortage of oxygen that is needed for cellular metabolism.

The present synergistic composition exhibit immunomodulatory, neuroprotective, cardioprotective, cytoprotective, anti-ageing, anti-cell death (apoptosis) effects.

The signs and symptoms are not limited to hepatic ischemia-reperfusion injury, ischaemic stroke, transient ischaemic attack (TIA), chronic ischaemic heart disease (IHD), obstructive pulmonary disease (OPD), pain, tissue injury, nerve damage, organ failure, a condition requiring reduction in blood pressure, pulmonary hypertension, tachycardia, myocardial ischemia, coronary artery disease, myocardial infarction (MI), cystic fibrosis, cancer, cancer-related cachexia, diabetes, type 2 diabetes and neuropathy, influenza, parainfluenza, respiratory catarrh, a bronchitis of viral etiology, Rhino- and adenoviral infection; mumps, measles; diseases caused by viruses of simple herpes I or herpes simplex type II (herpes lips, facial skin, mucous membranes of the oral cavity, skin, eye herpes), nerve injury, oxidative stress, inflammation, hypoxia, brain cell death and oxidative stress, aortic stiffness, arterial aging, arthrosclerosis, arthritis, myocardial inflammation, aerobic endurance, retinal dysfunction in light-induced degeneration, kidney stones, kidney failure, Lesch-Nyhan syndrome, Alzheimer's disease, Parkinson disease cognitive disorder, high fat, obesity, stem cell function, pregnancy-induced hypertension, chemotaxis and phagocytic impairment in immunological disorders, cerebrovascular diseases, aggregation disorders, fertility and reproductive disorders, erectile dysfunction.

In another embodiment, the invention provides synergistic bioactive compositions for enhancing cellular energy. Particularly the composition is targeted in the treatment of liver diseases, where it increases hepatic NAD$^+$/NADH ratio and restores intrahepatic energy/ATP level that subsequently provides energy for repairing and regeneration of damaged hepatocytes.

Concisely, the inosine monophosphate provides the raw material for synthesis of ATP, whereas nicotinamide precursors induce NAD$^+$/NADH involved in the tricarboxylic acid cycle, catalyze biochemical reactions that generate ATP, and thus contribute to a substantial increase in turnover of ATP.

The present composition has a protective effect on liver function. It improves liver metabolism and facilitates recovery of damaged liver.

The liver diseases include but are not limited to liver ischemia-reperfusion, liver transplantation, hepatic failure after shock, liver surgery, liver reperfusion injury, liver dysfunction, liver infection, liver failure, liver damage, hepatitis, liver cirrhosis, fatty liver dystrophy, including those caused by alcohol or drugs.

In some embodiment, the invention provides a synergistic composition comprising a combination of IMP and NMN or NR that increases metabolic turnover and leads to an increase in intrahepatic ATP content. Restoring intrahepatic ATP levels by administration of effective dose of the present synergistic combination greatly ameliorates reperfusion injury and restores the protective effects of ischemic preconditioning.

Further the present composition acts as an antioxidant, wherein the inosine produces uric acid that is a natural antioxidant and a peroxynitrite scavenger with potential benefits to patients with multiple sclerosis (MS). The administration of present inosine composition raises the levels of uric acid that subsequently slows down the progression of MS.

In another embodiment, the present invention provides an effective amount of bioactives or biomolecules or biochemicals or nutrients in an amount sufficient to prevent, treat, reduce, and/or ameliorate the symptoms and/or underlying causes of ATP deficiency or metabolic dysfunction.

In the context of the present invention, the terms "treatment" and the like refer to alleviate, mitigate, prophylaxis, attenuate, manage, regulate, modulate, control, minimize, lessen, decrease, down regulate, up regulate, improve, moderate, prevent, inhibit, stabilize, ameliorate or cure, heal the indications of metabolic dysfunction particularly liver dysfunction. The treatment further includes delaying or reversing or preventing or reducing the development or progression or formation or occurrence of conditions or indications related to metabolic dysfunction such as liver diseases.

The 'subject in need thereof' pertains to a subject preferably mammal, more preferably a human with pre-existing liver disease or a subject to whom the composition is administered to prevent occurrence of liver dysfunction.

The therapeutically effective amount of bio-actives will vary depending upon the subject and disease condition being treated, the weight and age of the subject, the severity of the disease condition, the manner of administration and the like, which can readily be determined by one of ordinary skill in the art.

Thus, a "therapeutically effective" amount is an amount that reduces the risk, potential, possibility or occurrence of a disease or disorder, or provides some alleviation, mitigation, and/or reduction of at least one indicator/biomarker (e.g., blood or serum CRP level), and/or decrease in at least one clinical symptom of a disease or disorder (such as liver dysfunction, liver damage).

An effective dose is a dose that gives desirable therapeutic outcome without side effects. According to the invention, the effective dose for oral administration is in the range of 100 to 500 mg, preferably 150-400 mg and administered daily once or twice or thrice based on the intensity of symptoms or indications.

In another embodiment, the invention relates to a synergistic composition which is prepared in a manner well known in the pharmaceutical art, and administered by a variety of routes, depending upon whether local or systemic treatment is desired and upon the area to be treated. Therapeutic (prescription) supplements are generally administered by the oral or parenteral routes for the treatment of indications including metabolic liver diseases such as liver failure, liver dysfunctions, liver injuries.

The therapeutic administration of compositions of the present invention may be in conjunction with other therapies.

In one embodiment, the present composition is administered to a subject in a form suitable for oral use, such as a tablet, capsule (in the form of delayed release, extended release, sustained release, enteric coated release), hard gelatin capsules, soft gelatin capsules in an oily vehicle, granules for sublingual use, effervescent tablets, aqueous or oily solution, suspension or emulsion, encapsulate, matrix, coat, beadlets, nanoparticles, caplet, granule, particulate, agglomerate, spansule, chewable tablet, lozenge, troche, solution, suspension, rapidly dissolving film, elixir, gel, or syrup. In another embodiment, the composition is formulated for parenteral use including intravenous, subcutaneous, intramuscular, intravascular or infusion routes of administration.

In a preferred embodiment, the nutritional composition/formulation is formulated for oral administration. Specifically, the solid nutritional compositions are in the form of tablets, capsules, pills, hard capsules filled with liquids or solids, soft capsules, sachets, powders, granules, suspensions, solutions or modified release formulations.

The term "pharmaceutically acceptable salt" refers to a salt prepared from pharmaceutically acceptable non-toxic acids or bases, halides, sulphates, phosphates, nitrate, metal ions, minerals, chelates, complex, esters, oxide, amines which are well known in the art.

As used herein, the term "pharmaceutically acceptable carriers/vehicles/diluents or excipients" is intended to mean, without limitation, any adjuvants, carriers, excipients, sweetening agents, diluents, preservative, dye/colorants, flavor enhancers, surfactants, wetting agents, dispersing agents, suspending agents, complexing agents, stabilizers, isotonic agent, solvent, emulsifier, encapsulating agent, polymers, coating agent, wax, encapsulating polymeric delivery systems. Excipients may also include, antiadherents, antioxidants, binders, pH-modifier, solvents, coatings, compression aids, disintegrants, emollients, fillers (diluents), film formers, fragrances, glidants (flow enhancers), lubricants, preservatives, sorbents, anticaking agent, food additives, or waters of hydration.

In some embodiment of the invention, the diluents are selected from starches, hydrolyzed starches, partially pregelatinized starches, anhydrous lactose, cellulose powder, lactose monohydrate, and sugar alcohols such as sorbitol, xylitol and mannitol, silicified microcrystalline cellulose, ammonium alginate, calcium carbonate, calcium lactate, dibasic calcium phosphate (anhydrous/dibasic dehydrate/tribasic), calcium silicate, calcium sulfate, cellulose acetate, corn starch, pregelatinized starch, dextrin, β-cyclodextrin, dextrates, dextrose, erythritol, ethylcellulose, fructose, fumaric acid, glyceryl palmitostearate, magnesium carbonate, magnesium oxide, maltodextrin, maltose, medium-chain triglycerides, polydextrose, polymethacrylates, sodium alginate, sodium chloride, sterilizable maize, sucrose, sugar spheres, talc, trehalose, xylitol, vehicles like petrolatum, dimethyl sulfoxide and mineral oil or the like.

In some embodiment of the invention, the amount of diluent in the nutritional composition/formulation is present in the range of 1% to 30% by weight of the total composition/formulation.

In a further embodiment, the binder is selected from disaccharides such as sucrose, lactose, polysaccharides and their derivatives like starches, cellulose or modified cellulose such as microcrystalline cellulose and cellulose ethers such as hydroxypropyl cellulose (HIPC); hydroxypropyl methyl cellulose (HPMC); sugar alcohols such as xylitol, sorbitol or mannitol; protein like gelatin; synthetic polymers such as polyvinylpyrrolidon (PVP), polyethylene glycol (PEG), starch, acacia, agar, alginic acid, calcium carbonate, calcium lactate, carbomers, carboxymethylcellulose sodium, carrageenan, cellulose acetate phthalate, chitosan, copovidone, corn starch, pregelatinized starch, cottonseed oil, dextrates, dextrin, dextrose, ethylcellulose, guar gum, hydrogenated vegetable oil, mineral oil, hydroxyethyl cellulose, hydroxymethyl cellulose hydroxyl ethylmethyl cellulose, hydroxypropyl cellulose, inulin, cellulose, methyl cellulose, polyvinylpyrrolidone and polyethylene glycol, lactose, liquid glucose, hypromellose, magnesium aluminum silicate, maltodextrin, maltose, methyl-cellulose, microcrystalline cellulose, pectin, poloxamer, polydextrose, polymethacrylates, povidone, sodium alginate, stearic acid, sucrose, sunflower oil, various animal vegetable oils, and white soft paraffin, paraffin, flavorants, colourants and wax.

In some embodiment of the invention, the amount of binder in the nutritional composition/formulation is present in the range of 0.1% to 30% by weight of the composition/formulation.

Further according to the invention, the lubricant is selected from magnesium stearate, zinc stearate, calcium stearate, glycerin monostearate, glyceryl behenate, glyceryl palmitostearate, hydrogenated castor oil, hydrogenated vegetable oil, light mineral oil, magnesium lauryl sulfate, medium-chain triglycerides, mineral oil, myristic acid, palmitic acid, poloxamer, polyethylene glycol, sodium benzoate, sodium chloride, sodium lauryl sulfate, sodium stearyl fumarate, stearic acid, talc, potassium benzoate, sodium oleate, sodium stearate, sodium acetate, sodium chloride, stearic acid, sodium stearyl fumarate, and talc or the like.

In some embodiment of the invention, the amount of lubricant in the nutritional composition/formulation is present in the range of 0.1% to 5% by weight of the total composition/formulation.

In some embodiment of the invention, the solubilizing agent is selected from polysorbate 80, sodium lauryl sulfate, anionic emulsifying wax, nonionic emulsifying wax, glyceryl monooleate, phospholipids, polyoxyethylene alkyl ethers, polyoxyethylene castor oil derivatives, polyoxyethylene sorbitan fatty acid esters, polyoxyethylene stearates, polyoxylglycerides, sorbitan esters, triethyl citrate, vitamin E, polyethylene glycol succinate, microcrystalline cellulose, carboxymethylcellulose sodium, diethanolamine, ethylene glycol palmitostearate, glycerin monostearate, hypromellose, hypromellose, acetate succinate, lecithin, polyethylene alkyl ethers, aluminum oxide, poly(methylvinyl ether/maleic anhydride), calcium carbonate, crospovidone, cyclodextrins, fructose, hydroxpropyl betadex, oleyl alcohol, povidone, benzalkonium chloride, benzethonium chloride, benzyl alcohol, benzyl benzoate, cetylpyridinium chloride, inulin, meglumine, poloxamer, pyrrolidone, sodium bicarbonate, starch, stearic acid, sulfobutylether beta cyclodextrin, tricaprylin, triolein, docusate sodium, glycine, alcohol, self-emulsifying glyceryl monooleate, cationic benzethonium chloride, cetrimide, xanthan gum, lauric acid, myristyl alcohol, butylparaben, ethylparaben, methylparaben, propylparaben, sorbic acid or the like. The amount of solubilizing agent or surfactant in the nutritional composition/formulation of the present invention ranges from 0.1% to 5% by weight of the composition/formulation.

In some embodiment of the invention, the glidant is selected from colloidal silicon dioxide, magnesium stearate, fumed silica (colloidal silicon dioxide), starch, talc, calcium phosphate tribasic, cellulose powdered, hydrophobic colloidal silica, magnesium oxide, zinc stearate, magnesium silicate, magnesium trisilicate, silicon dioxide, starch, methyl cellulose, agar, bentonite, xanthan gum, sodium croscarmellose, sodium starch glycolate, cross linked sodium carboxymethylcellulose or the like.

In some embodiment of the invention, the amount of glidant present in the nutritional composition/formulation ranges from 0.1% to 5% by weight of the total composition/formulation.

In some embodiment, the solvent is selected from water, alcohol, isopropyl alcohol, propylene glycol, mineral oil, benzyl alcohol, benzyl benzoate, flavored glycol, carbon dioxide, castor oil, corn oil (maize), cottonseed oil, dimethyl ether, albumin, dimethylacetamide, ethyl acetate, ethyl lactate, medium-chain triglycerides, methyl lactate, olive oil, peanut oil, polyethylene glycol, polyoxyl, castor oil, propylene carbonate, pyrrolidone, safflower oil, sesame oil, soybean oil, sunflower oil, water-miscible solvents, organic polar or non-polar solvents or mixtures thereof. In some embodiment of the invention, the solvent in the nutritional composition/formulation is present in a quantity sufficient to 100% by weight of the composition/formulation.

The additional additives include polymer, a plasticizer, a sweetener, and a powdered flavor, preservative, colorant, surfactant and other excipients. The powdered flavor composition includes a flavourant associated with a solid carrier. Coating materials such as synthetic polymers, shellac, zein, corn protein or other polysaccharides, gelatin, fatty acids, waxes, shellac, plastics, plant fibers and like thereof are used. The additives are used in the range of 1 to 30% w/w of unit dose.

In some embodiment, the present invention provides synergistic nutritional compositions, wherein the diluent is present in the range of 1 to 30%; the binder is present in the range of 0.1 to 20%; the lubricant is present in the range of 0.1 to 5.0%; the glidant is present in the range of 0.1 to 5.0%; the additive is present in the range of 1 to 20%; the surfactant is present in the range of 0.1 to 5.0% by weight of total composition.

Notably, the instant synergistic composition is non-hazardous, non-toxic and safe for human consumption without any adverse effects, therefore the instant composition can also be used under preventive therapy in healthy subjects.

The present nutritional composition is used to manage ATP deficiency conditions in the subject in need by administration of the remedy either to prevent occurrence or for pre-existing cause of energy-related dysfunctions like liver diseases/dysfunctions.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention While in the foregoing specification, this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entireties. The present invention may be embodied in other specific forms without departing from the spirit or essential attributes thereof and, accordingly, reference should be made to the appended claims, rather than to the foregoing specification, as indicating the scope of the invention.

The invention may be further illustrated by the following examples, which are for illustrative purposes only and should not be construed as limiting the scope of the invention in anyway.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes or alterations which come within the ambit of equivalency are intended to be encompassed therein.

EXAMPLES

Example 1 i. Composition 1a: Synergistic Blend

| Ingredient | w/w % |
|---|---|
| Inosine 5'-monophosphate disodium salt hydrate | 40-90% |
| NAD$^+$ Precursors | 10-35% |

Proprietary blend MTORSIRT™ contains Inosine monophosphate (IMP) in the range of 40%-90 wt. %+NAD$^+$ precursors in the range of 10%-35 wt. %.

The therapeutic proprietary composition is a blend of the active ingredients with the proportionate excipients filled in soft gel, hard gel or veg capsule by known technique. Further, the blend with the proportionate excipients is compressed to get tablet in coated or uncoated form.

ii. Composition 1b: Synergistic Blend

| Ingredients | w/w % |
|---|---|
| Inosine 5'-monophosphate disodium salt hydrate | 50-90% |
| Nicotinamide riboside chloride | 10-35% | iii. Composition 1c: Synergistic Blend

| Ingredients | w/w % |
|---|---|
| Inosine 5'-monophosphate disodium salt hydrate | 50-90% |
| β-Nicotinamide mononucleotide | 15-35% | iv. Composition 2: Tablet/Capsule

| Ingredients | w/w % unit dose |
|---|---|
| Inosine 5'-monophosphate disodium salt hydrate | 73 ± 5% |
| β-Nicotinamide mononucleotide | 18 ± 5% |
| Excipients | 5-10% |
| Average weight (%) | 100% |
| Average weight in mg | 325-350 mg | v. Composition 3: Tablet/Capsule

| Ingredients | w/w % unit dose |
|---|---|
| Inosine 5'-monophosphate disodium salt hydrate | 65 ± 8% |
| β-Nicotinamide mononucleotide | 15 ± 5% |
| Excipients | 10-20% |
| Average weight (%) | 100% |
| Average weight in mg | 350-400 mg | vi. Composition 4: Tablet/Capsule

| Ingredients | w/w % unit dose |
|---|---|
| Inosine 5'-monophosphate disodium salt hydrate | 60 ± 10% |
| β-Nicotinamide mononucleotide | 30 ± 5% |
| Excipients | 5-20% |
| Average weight (%) | 100% |
| Average weight in mg | 200-250 mg | vii. Composition 5: Tablet/Capsule

| Ingredients | w/w % unit dose |
|---|---|
| Inosine 5'-monophosphate disodium salt hydrate | 60 ± 10% |
| Nicotinamide riboside chloride | 30 ± 5% |
| Excipients | 5-20% |
| Average weight (%) | 100% |
| Average weight in mg | 150-200 mg | viii. Composition 6: Tablet/Capsule

| Ingredients | w/w % unit dose |
|---|---|
| Inosine monophosphate sodium salt hydrate | 73 ± 5% |
| Nicotinamide riboside chloride | 15 ± 5% |
| Excipients | 20 ± 5% |
| Average weight (%) | 100% |
| Average weight in mg | 325-350 mg | ix. Composition 7: Tablet/Capsule

| Ingredients | w/w % unit dose |
|---|---|
| Inosine monophosphate sodium salt hydrate | 73 ± 5% |
| β-Nicotinamide mononucleotide | 18 ± 5% |
| Diluents | 1-10% |
| Binders | 0.5-5% |
| Glidants | 0.5-5% |
| Lubricants | 0.5-5% |
| Additives | 1-10% |
| Solvents | QS | x. Composition 8: Tablet/Capsule

| Ingredient | mg per unit dose |
|---|---|
| Inosine monophosphate sodium salt hydrate | 250 |
| β-Nicotinamide mononucleotide | 50 |
| Microcrystalline Cellulose | 1-10 |
| Silicon dioxide | 1-10 |

-continued x. Composition 8: Tablet/Capsule

| Ingredient | mg per unit dose |
|---|---|
| Hydroxypropyl Methylcellulose | 1-10 |
| Magnesium Stearate | 1-5 |
| PVP K-30 | 1-5 |
| Talc | 1-5 |
| Tween 80 | 1-10 |
| Mannitol | 1-10 |
| IPA | QS |
| Water | QS |
| Average weight | 325-350 mg |

Example 2: Cell Line Study

In Vitro Evaluation of the Therapeutic Effect of Test Substances on Cellular Energy by Measuring Cellular ATP Levels in Human Hepatocyte Cell Line The test substances were evaluated for their in vitro effect on cellular energy by measuring cellular ATP levels in human Hepatocytes (HepG2) cell line. In the given experimental conditions, treatment with the test substances improved cellular ATP levels in vitro. [*J Immunol Methods;* 1986; 89: 271-277]; [*Proc Natl Acad Sci USA;* 2009; 106: 15651-15656].

Procedure i. Outline of the Method

The in vitro cytotoxicity study was performed on HepG2 (Human Hepatocyte) cell line to find a nontoxic concentration of the test substances by MTT colorimetric assay and evaluate their potential on cellular respiration by measuring cellular ATP levels.

ii. Preparation of Test Solution

About 10 mg of all the test substances (as indicated in Table 1) were separately dissolved with 100 μl of Dimethyl sulfoxide (DMSO) and volume was made up with Dulbecco's Modified Eagle Medium-High glucose (DMEM-HG) supplemented with 2% inactivated Fetal Bovine Serum (FBS) to obtain a stock solution of 1 mg/ml concentration and sterilized by 0.22p, syringe filtration. Serial two-fold dilutions were prepared from the stock for carrying out further studies.

iii. Cell Line and Culture Medium:

Cell line was cultured in DMEM-HG supplemented with 10% inactivated FBS, penicillin (100 IU/ml), streptomycin (100 μg/ml) and amphotericin B (5 μg/ml) in a humidified atmosphere of 5% $CO_2$ at 37° C. until confluent. The cells were dissociated with TPVG solution (0.2% trypsin, 0.02% EDTA, 0.05% glucose in PBS). The stock cultures were grown in 25 $cm^2$ culture flasks and all experiments were carried out in 96 well microtitre plates (Tarsons India Pvt. Ltd., Kolkata, India).

iv. Cytotoxicity Studies

The monolayer cell culture was trypsinized and the cell count was adjusted to $1.0×10^5$ cells/ml using Ham's F12 medium containing 10% FBS to obtain a cell suspension. To each well of the 96 well microtitre plate, 0.1 ml of the diluted cell suspension was added. After 24 hours, when a partial monolayer was formed, the supernatant was flicked off, the monolayer was washed once with medium and 100 μl of different concentrations of test substances were added. The plate was then incubated at 37° C. for 72 hours in a 5% $CO_2$ atmosphere, and microscopic examination was carried out and observations were noted every 24 hours.

iv. 1. MTT Assay

After 72 hours of incubation, the drug solutions in the wells were discarded and 50 μl of MTT in PBS was added to each well. The plate was gently shaken and incubated for 3 hr at 37° C. in a 5% $CO_2$ atmosphere. The supernatant was removed and 100 μl of 2-propanol was added and the plate was gently shaken to solubilize the formed formazan. The absorbance was measured using a microplate reader at a wavelength of 540 nm. The percentage growth inhibition was calculated using the standard formula. The concentration of test substances needed to inhibit the growth of the cell by 50% i.e., $CTC_{50}$ values were generated from the dose-response curves.

v. Estimation of Cellular Respiration by Measuring Cellular ATP Levels

HepG2 cells were trypsinized from stock culture flasks and the cell count was adjusted to $1.0×10^5$ cells/ml to obtain a cell suspension that was seeded into a 96-well plate. After 24 hours, cell cultures achieved 70-80% confluency and were treated with different nontoxic concentrations of test substances. After 2 hours of treatment, the plate was washed with phosphate buffer saline. The cellular ATP levels determination was performed according to the instructions given in the kit manual (SIGMA, #MAK190). At the end of the experiment, the optical density was read at 570 nm using microplate reader. From the absorbance values, the cellular ATP levels were estimated using kit protocol and the concentration of cellular ATP in treated groups were determined in comparison to the control groups.

vi. Study Design

TABLE 1

Group, dose and treatment

| Gr. No. | Group | Dose and Treatment | Parameters Analysed |
|---|---|---|---|
| G1 | Cell Control | No treatment | Cellular ATP levels |
| G2 | Positive Control ($H_2O_2$-20 μM) | Cells were treated with $H_2O_2$ | |
| G3 | IMP (500 μg/ml) | Cells were treated with test substance (IMP) | |
| G4 | NMN (250 μg/ml) | Cells were treated with test substance (NMN) | |
| G5 | IMP + NMN (500 μg/ml) | Cells were treated with test substances (IMP + NMN) | |
| G6 | IMP (500 μg/ml) + $H_2O_2$ (20 μM) | Cells were treated with test substance (IMP) along with $H_2O_2$ | |
| G7 | NMN (250 μg/ml) + $H_2O_2$ (20 μM) | Cells were treated with test substance (NMN) along with $H_2O_2$ | |
| G8 | IMP + NMN (500 + 250μg/ml) + $H_2O_2$ (20 μM) | Cells were treated with test substance (IMP + NMN) along with $H_2O_2$ | |

TABLE 2

Cytotoxicity properties of test substances against HepG2 cell line.

| Sr. No | Name of Test Substance (Group No.) | Test Conc. (μg/ml) | % Inhibition | CTC 50 in μg/ml |
|---|---|---|---|---|
| 1. | Inosine-5'-Monophosphate (IMP) (G3) | 1000 | 45.13 ± 3.24 | >1000 |
| | | 5000 | 35.47 ± 1.04 | |
| | | 250 | 16.07 ± 1.6 | |
| | | 125 | 9.35 ± 1.07 | |

TABLE 2-continued

Cytotoxicity properties of test substances against HepG2 cell line.

| Sr. No | Name of Test Substance (Group No.) | Test Conc. (µg/ml) | % Inhibition | CTC 50 in µg/ml |
|---|---|---|---|---|
| 2. | Nicotinamide-Monophosphate (NMN) (G4) | 62.5 | 5.71 ± 0.66 | 415.92 ± 8.99 |
|  |  | 1000 | 76.59 ± 0.54 |  |
|  |  | 500 | 59.95 ± 1.78 |  |
|  |  | 250 | 30.51 ± 0.38 |  |
|  |  | 125 | 21.59 ± 1.89 |  |
|  |  | 62.5 | 2.26 ± 1.49 |  |
| 3. | IMP + NMN (2:1) (G5) | 1000 | 76.59 ± 0.54 | 679.95 ± 6.57 |
|  |  | 500 | 59.95 ± 1.78 |  |
|  |  | 250 | 30.51 ± 0.38 |  |
|  |  | 125 | 21.59 ± 1.89 |  |
|  |  | 62.5 | 2.26 ± 1.49 |  |

TABLE 3

Effect of test substances on cellular ATP levels in HepG2 cells.

| Sl. No. | Group No. | OD values (treated)-OD values (Blank)@ 405 nm | Cellular ATP (nmoles) | Percentage enhancement of cellular ATP levels over control |
|---|---|---|---|---|
| 1. | G1 | 0.0 ± 0.0 | 0.0 ± 0.0 | 0.00 ± 0.00 |
| 2. | G2 | 0.007 ± 0.012 | 0.86 ± 0.02 | 0.00 ± 0.00 |
| 3. | G3 | 0.019 ± 0.03 | 2.82 ± 0.16 | 7.64 ± 1.26 |
| 4. | G4 | 0.026 ± 0.02 | 4.43 ± 0.23 | 13.97 ± 1.25 |
| 5 | G5 | 0.044 ± 0.04 | 7.06 ± 0.13 | 24.22 ± 2.12 |
| 6 | G6 | 0.099 ± 0.06 | 16.26 ± 0.93 | 60.27 ± 3.85 |
| 7 | G7 | 0.051 ± 0.05 | 8.28 ± 0.65 | 29.01 ± 4.25 |
| 8 | G8 | 0.138 ± 0.08 | 22.78 ± 1.6 | 85.64 ± 8.13 |

Discussion and Conclusion:

The test substances were evaluated for their cytotoxicity with different concentrations ranging from 62.5 µg/ml to 1000 µg/ml. The $CTC_{50}$ value was found to be more than 1000 µg/ml for IMP. For NMN, the $CTC_{50}$ value is 415±8.99 and for the combination of IMP+NMN the $CTC_{50}$ value is 679.95±6.57. Hence, the test concentrations of 250 µg/ml of NMN and 500 µg/ml of IMP were taken for further studies. For the test substance IMP+NMN, the concentration was taken 500 µg/ml.

The percentage enhancement of cellular ATP levels was found to be 7.64±1.26 and 13.97±1.25 for (G3) IMP and (G4) NMN respectively. The combination of the test substances (G5) dissolved in the ratio of 2:1, showed 24.22±2.12% enhancement in ATP levels over the hydrogen peroxide control.

In combination with Hydrogen peroxide (20 µM), both the test substances (G6) IMP, (G7) NMN and the combination (G8) increased the cellular ATP levels significantly.

We claim:

1. A synergistic bioactive composition for enhancing intracellular ATP levels in a subject suffering from liver diseases, the synergistic bioactive composition consisting of:
   an exogenous blend of inosine 5' monophosphate disodium salt hydrate and nicotinamide riboside chloride or β-nicotinamide mononucleotide along with pharmaceutically acceptable excipients, wherein the inosine 5' monophosphate disodium salt hydrate and the nicotinamide riboside chloride or the β-nicotinamide mononucleotide are present in a weight ratio of 1:0.2 to 1:0.5.

2. The synergistic bioactive composition as claimed in claim 1, wherein the inosine 5' monophosphate disodium salt hydrate is present in a range of 40% to 90% by weight of the total composition.

3. The synergistic bioactive composition as claimed in claim 1, wherein the nicotinamide riboside chloride or the β-nicotinamide mononucleotide are present in a range of 10% to 35% by weight of the total composition.

4. The synergistic bioactive composition as claimed in claim 1, wherein an oral administration of an effective dose of the composition increases intracellular ATP levels in the subject suffering from the liver diseases or dysfunctions.

5. A synergistic bioactive composition consisting of an exogenous blend of inosine 5'-monophosphate disodium salt hydrate and nicotinamide riboside chloride in a ratio of 1:0.2 to 1:0.5 along with pharmaceutically acceptable excipients.

6. The synergistic bioactive composition as claimed in claim 5, wherein the inosine 5'-monophosphate disodium salt hydrate is present in a range of 50-90% and the nicotinamide riboside chloride is present in a range of 10-35% by weight of the total composition along with the pharmaceutically acceptable excipients.

7. A synergistic bioactive composition for enhancing intracellular ATP levels in a subject suffering from liver diseases, the synergistic bioactive composition consisting of an exogenous blend of inosine 5'-monophosphate disodium salt hydrate and β-nicotinamide mononucleotide in a ratio of 1:0.25 to 1:0.5 along with pharmaceutically acceptable excipients.

8. The synergistic bioactive composition as claimed in claim 7, wherein the inosine 5'-monophosphate disodium salt hydrate is present in a range of 50-90% and the β-nicotinamide mononucleotide is present in a range of 15-35% by weight of the total composition along with the pharmaceutically acceptable excipients.

\* \* \* \* \*